(12) United States Patent
Ceccarelli et al.

(10) Patent No.: US 7,173,133 B2
(45) Date of Patent: Feb. 6, 2007

(54) DIAZA-SPIROPIPERIDINE DERIVATIVES

(75) Inventors: Simona Maria Ceccarelli, Basel (CH); Synese Jolidon, Blauen (CH); Emmanuel Pinard, Linsdorf (FR); Andrew William Thomas, Birsfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 217 days.

(21) Appl. No.: 11/028,281

(22) Filed: Jan. 3, 2005

(65) Prior Publication Data
US 2005/0154001 A1 Jul. 14, 2005

(30) Foreign Application Priority Data
Jan. 8, 2004 (EP) .................. 04100033

(51) Int. Cl.
C07D 471/10 (2006.01)
C07D 405/14 (2006.01)
(52) U.S. Cl. .......................... 546/16; 546/15
(58) Field of Classification Search ............ 546/16, 546/15
See application file for complete search history.

(56) References Cited

FOREIGN PATENT DOCUMENTS

| WO | WO 01/94346 A1 | 12/2001 |
|---|---|---|
| WO | WO 03/010138 A2 | 2/2003 |
| WO | WO 03/049741 A1 | 6/2003 |

OTHER PUBLICATIONS

Lewis D. A. et al., Neuron, 2000, vol. 28, pp. 325-334.
Vandenberg R. J., et al., Exp. Opin. Ther. Targets, 2001, vol. 5(4) pp. 507-518.
Nakazato A. et al., 2000, Exp. Opin. Ther. Patents vol. 10(1) pp. 75-98.
Sharma T., Br. J. Psychiatry, 1999, vol. 174 (Suppl. 28) pp. 44-51.
Javitt D.C., 1999, Biol. Psychiatry, vol. 45, pp. 668-679.
Mohn A. R. et al., 1999, Cell, vol. 98, pp. 427-436.
Bliss, T. V. et al., 1993, Nature, vol. 361 pp. 31-39.
Tang J. P. et al., 1999, Nature, vol. 401, pp. 63-69.
Gainetdinov R. R. et al., 2002, Trends in Pharm. Sci. vol. 23(8) pp. 367-373.
Lopez-Corcuera B. et al., 2001, Mol. Mem. Biol. vol. 18, pp. 13-20.
Bergeron R. et al., 1998, Proc. Natl. Acad. Sci. USA, vol. 95, pp. 15730-15734.
Chen, L. et al., 2003, J. Neurophysiol. vol. 89(2) pp. 691-703.
Armer R. E. et al., 2001, Exp. Opin. Ther. Patents vol. 11(4) pp. 563-572.
Pralong E. T. et al., 2002, Prog. Neurobiol. vol. 67, pp. 173-202.
Carlsson M. L. 1998, J. Neurol. Transm. vol. 105, pp. 525-535.
Jonas Bortrom, et al., *A 3d qsar study on a set of dopamine d4 receptor antagonists*, J.Chem. Inf. Comp. Sci, vol. 43, pp. 1020-1027 (2003), XP002272148.

*Primary Examiner*—Charanjit S. Aulakh
(74) *Attorney, Agent, or Firm*—George W. Johnston; Patricia S. Rocha-Tramaloni; Kimberly J. Prior

(57) ABSTRACT

The present invention relates to compounds of formula

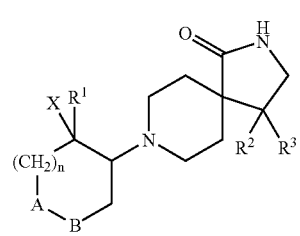

wherein
A-B is —CH$_2$—CH$_2$—, —CH$_2$—O— or —O—CH$_2$—;
X is hydrogen or hydroxy;
R$^1$ is aryl, optionally substituted by one or two substituents selected from the group consisting of halogen, lower alkyl, cyano, CF$_3$, —OCF$_3$, lower alkoxy, —SO$_2$-lower alkyl and heteroaryl;
R$^2$ is aryl, optionally substituted by one or two substituents selected from the group consisting of halogen, lower alkyl, CF$_3$, and lower alkoxy;
R$^3$ is hydrogen or lower alkyl;
n is 0, 1 or 2;
or a pharmaceutically active salt thereof.

The compounds of the invention may be used in the treatment of neurological and neuropsychiatric disorders.

52 Claims, No Drawings

DIAZA-SPIROPIPERIDINE DERIVATIVES

FIELD OF THE INVENTION

The present invention relates to the treatment of CNS disorders such as schizophrenia and Alzheimer's disease. More particularly, the invention relates to inhibition of GlyT-1 and GlyT-2.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, *Neuron*, 2000, 28:325–33). For decades research has focused on the "dopaminergic hyperactivity" hypothesis which has led to therapeutic interventions involving blockade of the dopaminergic system (Vandenberg R J and Aubrey K R., *Exp. Opin. Ther. Targets*, 2001, 5(4): 507–518; Nakazato A and Okuyama S, et al., 2000, *Exp. Opin. Ther. Patents*, 10(1): 75–98). This pharmacological approach poorly address negative and cognitive symptoms which are the best predictors of functional outcome (Sharma T., *Br. J. Psychiatry*, 1999, 174(suppl. 28): 44–51).

A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly in healthy volunteers, PCP-induced psychotomimetic action incorporates positive and negative symptoms as well as cognitive dysfunction, thus closely resembling schizophrenia in patients (Javitt D C et al., 1999, *Biol. Psychiatry*, 45: 668–679 and refs. herein). Furthermore transgenic mice expressing reduced levels of the NMDAR1 subunit displays behavioral abnormalities similar to those observed in pharmacologically induced models of schizophrenia, supporting a model in which reduced NMDA receptor activity results in schizophrenia-like behavior (Mohn A R et al., 1999, *Cell*, 98: 427–236).

Glutamate neurotransmission, in particular NMDA receptor activity, plays a critical role in synaptic plasticity, learning and memory, such as the NMDA receptors appears to serve as a graded switch for gating the threshold of synaptic plasticity and memory formation (Hebb D O, 1949, *The organization of behavior*, Wiley, N.Y.; Bliss T V and Collingridge G L, 1993, *Nature*, 361: 31–39). Transgenic mice overexpressing the NMDA NR2B subunit exhibit enhanced synaptic plasticity and superior ability in learning and memory (Tang J P et al., 1999, *Nature*: 401–63–69).

Thus, if a glutamate deficit is implicate in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters by removing neurotransmitters from the extracellular space, can control their extracellular lifetime and thereby modulate the magnitude of the synaptic transmission (Gainetdinov R R et al, 2002, Trends in Pharm. Sci., 23(8): 367–373).

Glycine transporters, which form part of the sodium and chloride family of neurotransmitter transporters, play an important role in the termination of post-synaptic glycinergic actions and maintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., 2001, *Mol. Mem. Biol.*, 18: 13–20). Thus, one strategy to enhance NMDA receptor activity is to elevate the glycine concentration in the local microenvironment of synaptic NMDA receptors by inhibition of GlyT-1 transporter (Bergereon R. Et al., 1998, *Proc. Natl. Acad. Sci. USA*, 95: 15730–15734; Chen L et al., 2003, *J. Neurophysiol.*, 89 (2): 691–703).

Glycine transporters inhibitors are suitable for the treatment of neuroligical and neuropsychiatric disorders. The majority of diseases states implicated are psychoses, schizophrenia (Armer R E and Miller D J, 2001, *Exp. Opin. Ther. Patents*, 11 (4): 563–572), psychotic mood disorders such as severe major depressive disorder, mood disorders associated with psychotic disorders such as acute mania or depression associated with bipolar disorders and mood disorders associated with schizophrenia, (Pralong E T et al., 2002, *Prog. Neurobiol.*, 67: 173–202), autistic disorders (Carlsson M L, 1998, *J. Neural Transm.* 105: 525–535), cognitive disorders such as dementias, including age related dementia and senile dementia of the Alzheimer type, memory disorders in a mammal, including a human, attention deficit disorders and pain (Armer R E and Miller D J, 2001, *Exp. Opin. Ther. Patents*, 11 (4): 563–572).

Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

SUMMARY OF THE INVENTION

The present invention provides compounds of formula

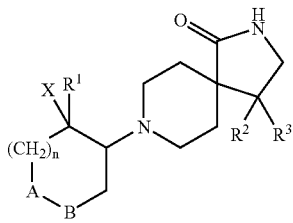

I wherein

A-B is —CH$_2$—CH$_2$—, —CH$_2$—O— or —O—CH$_2$—;

X is hydrogen or hydroxy;

R$^1$ is aryl, optionally substituted by one or two substituents selected from the group consisting of halogen, lower alkyl, cyano, CF$_3$, —OCF$_3$, lower alkoxy, —SO$_2$-lower alkyl, and heteroaryl;

R$^2$ is aryl, optionally substituted by one or two substituents selected from the group consisting of halogen, lower alkyl, CF$_3$, and lower alkoxy;

R$^3$ is hydrogen or lower alkyl;

n is 0, 1 or 2;

or a pharmaceutically active salt thereof.

Furthermore, the invention includes all racemic mixtures, all their corresponding enantiomers and/or optical isomers.

The invention also provides processes for the manufacture of compounds of the invention, their enantiomers, and pharmaceutically acceptable salts. The invention further provides pharmaceutical compositions containing an effective amount of one or more compounds of formula I per se, or pharmaceutically acceptable salts thereof, and a pharmaceutically acceptable carrier and method for the manufacture of such compositions.

It has surprisingly been found that the compounds of the invention are good inhibitors of the glycine transporter 1 (GlyT-1), and that they have a good selectivity to glycine transporter 2 (GlyT-2) inhibitors. Thus the compounds of the invention are useful for the treatment of diseases related to activation of NMDA receptors via Glyt-1 inhibition.

The invention relates to the treatment of neurological and neuropsychiatric disorders with compounds of the invention. For example, the present invention provides methods for the treatment, control, or prevention of illnesses such as psychoses, disfunction in memory and learning, schizophrenia, dementia and other diseases in which cognitive processes are impaired, such as attention deficit disorders or Alzheimer's disease.

The preferred indications using the compounds of the present invention are schizophrenia, cognitive impairment and Alzheimer's disease.

DETAILED DESCRIPTION OF THE INVENTION

The following definitions of general terms used herein apply irrespective of whether the terms in question appear alone or in combination. It must be noted that, as used in the specification and the appended claims, the singular forms "a," "an," and "the" include plural forms unless the context clearly dictates otherwise.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1–4 carbon atoms.

The term "lower alkoxy" denotes a lower alkyl-O— group, where the lower alkyl part is as defined above.

The term "halogen" denotes chlorine, iodine, fluorine and bromine.

The term "aryl" denotes a monovalent cyclic aromatic hydrocarbon radical consisting of one or more fused rings in which at least one ring is aromatic in nature, for example phenyl or naphthyl.

The term "heteroaryl" denotes a cyclic aromatic hydrocarbon radical, containing one, two or three heteroatoms, selected from the group consisting of oxygen, sulphur or nitrogen, for example pyridyl, pyrazinyl, pyrimidinyl, pyridazinyl, triazinyl, thiazolyl, thienyl, furyl, pyrrolyl, imidazolyl, pyrazolyl, oxazolyl, isothiazolyl or isoxazolyl.

"Pharmaceutically acceptable," such as pharmaceutically acceptable carrier, excipient, etc. means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

The present invention provides compounds of formula

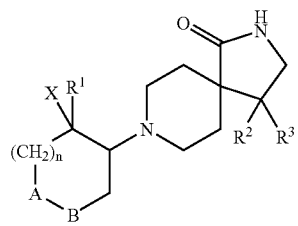

I wherein

A-B is —CH$_2$—CH$_2$—, —CH$_2$—O— or —O—CH$_2$—;

X is hydrogen or hydroxy;

R$^1$ is aryl, optionally substituted by one or two substituents selected from the group consisting of halogen, lower alkyl, cyano, CF$_3$, —OCF$_3$, lower alkoxy, —SO$_2$-lower alkyl, and heteroaryl;

R$^2$ is aryl, optionally substituted by one or two substituents selected from the group consisting of halogen, lower alkyl, CF$_3$, and lower alkoxy;

R$^3$ is hydrogen or lower alkyl;

n is 0, 1 or 2;

or a pharmaceutically active salt thereof.

Preferred compounds of formula I are those of formula

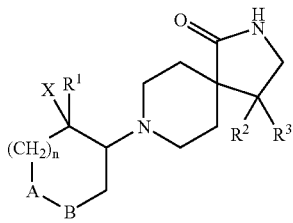

I wherein
A-B is —CH$_2$—CH$_2$— or —CH$_2$—O—. Among these compounds, preferred compounds are those in which R$^1$ is phenyl, optionally substituted by one or two substituents selected from the group consisting of halogen, lower alkyl, cyano, CF$_3$, —OCF$_3$, lower alkoxy, —SO$_2$-lower alkyl, and heteroaryl; particularly those compounds where R$^1$ is phenyl. Further preferred are compounds within this group where R$^2$ is phenyl, optionally substituted by one or two substituents selected from the group consisting of halogen and lower alkoxy. Within this group of compounds are preferred compounds in which R$^3$ is hydrogen, of which those having n is 1 are most preferred.

Thus, preferred compounds are compounds of formula I

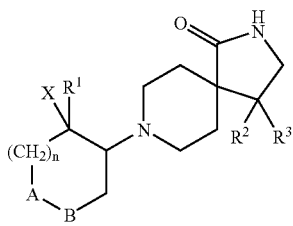

I wherein
A-B is —CH$_2$—CH$_2$— or —CH$_2$—O—;
X is hydrogen or hydroxy;
R$^1$ is phenyl, optionally substituted by one or two substituents selected from the group consisting of halogen, lower alkyl, cyano, CF$_3$, —OCF$_3$, lower alkoxy, —SO$_2$-lower alkyl, and heteroaryl,
R$^2$ is phenyl, optionally substituted by one or two substituents selected from the group consisting of halogen, and lower alkoxy;
R$^3$ is hydrogen;
n is 1;
or a pharmaceutically active salt thereof.

Most preferred are compounds, wherein n is 1 and A-B is —CH$_2$—CH$_2$—. Especially preferred compounds from this group are those, wherein R$^1$ and R$^2$ are both phenyl, optionally substituted by lower alkyl, halogen or CF$_3$, for example the following compounds:
  cis-rac-4-phenyl-8-(2-phenyl-cyclohexyl)-2,8-diaza-spiro[4.5]decan-1-one,
  cis-rac-4-phenyl-8-(2-p-tolyl-cyclohexyl)-2,8-diaza-spiro[4.5]decan-1-one,
  cis-rac-8-[2-(4-fluoro-phenyl)-cyclohexyl]-4-phenyl-2,8-diaza-spiro[4.5]decan-1-one,
  cis-rac-4-(4-fluoro-phenyl)-8-[2-(4-fluoro-phenyl)-cyclohexyl]-2,8-diaza-spiro[4.5]decan-1-one,
  cis-rac-4-(4-fluoro-phenyl)-8-[2-(4-trifluoromethyl-phenyl)-cyclohexyl]-2,8-diaza-spiro[4.5]decan-1-one,
  8-[2-(4-fluoro-phenyl)-2-hydroxy-cyclohexyl]-4-phenyl-2,8-diaza-spiro[4.5]decan-1-one,
  4-(4-fluoro-phenyl)-8-[2-(3-fluoro-phenyl)-2-hydroxy-cyclohexyl]-2,8-diaza-spiro[4.5]decan-1-one,
  4-(4-fluoro-phenyl)-8-[2-(2-fluoro-phenyl)-2-hydroxy-cyclohexyl]-2,8-diaza-spiro[4.5]decan-1-one,
  8-[2-(3-chloro-phenyl)-2-hydroxy-cyclohexyl]-4-(4-fluoro-phenyl)-2,8-diaza-spiro[4.5]decan-1-one or
  4-(4-fluoro-phenyl)-8-trans-(4-hydroxy-4-phenyl-tetrahydro-pyran-3-yl)-2,8-diaza-spiro[4.5]decan-1-one.

Also preferred within this group of compounds are those wherein n is 1.

Another group of preferred compounds are those in which A-B is —CH$_2$—O—. Within this group, compounds in which R$^1$ and R$^2$ are both phenyl, optionally substituted by lower alkyl, halogen or CF$_3$ are preferred, particularly compounds in which n is 1.

Another preferred group of compounds are compounds of formula I in which R$^2$ is phenyl, optionally substituted by one or two substituents, selected from the group consisting of halogen and lower alkoxy, for example, compounds where R$^2$ is phenyl.

Preferred are further compounds, wherein X is hydrogen. Among this group of compounds are those in which R$^1$ is phenyl, optionally substituted by one or two substituents selected from the group consisting of halogen, lower alkyl, cyano, CF$_3$, —OCF$_3$, lower alkoxy, —SO$_2$-lower alkyl, and heteroaryl. Also among this group are compounds in which R$^2$ is phenyl, optionally substituted by one or two substituents selected from the group consisting of halogen and lower alkoxy. Other preferred compounds are those in which R$^3$ is hydrogen. Also preferred are such compounds where R$^3$ is lower alky. Also within this group are compounds where n is 1. Compounds within this group having A-B as —CH$_2$—O— are preferred, as are compounds in which A-B is —CH$_2$—CH$_2$—.

The invention relates also to compounds, wherein X is hydroxy. Among this group of compounds are those in which R$^1$ is phenyl, optionally substituted by one or two substituents selected from the group consisting of halogen, lower alkyl, cyano, CF$_3$, —OCF$_3$, lower alkoxy, —SO$_2$-lower alkyl, and heteroaryl. Also among this group are compounds in which R$^2$ is phenyl, optionally substituted by one or two substituents selected from the group consisting of halogen and lower alkoxy. Other preferred compounds are those in which R$^3$ is hydrogen. Also preferred are such compounds where R$^3$ is lower alkyl. Also within this group are compounds where n is 1. Compounds within this group having A-B as —CH$_2$—O— are preferred, as are compounds in which A-B is —CH$_2$—CH$_2$—.

Objects of the present invention are further compounds, wherein n is 1 and A-B is —CH$_2$—O—.

Other compounds of the invention are compounds of formula I in which R$^1$ is phenyl, optionally substituted by one or two substituents selected from the group consisting of halogen, lower alkyl, cyano, CF$_3$, —OCF$_3$, lower alkoxy, —SO$_2$-lower alkyl, and heteroaryl. Also among this group are compounds in which R$^2$ is phenyl, optionally substituted by one or two substituents selected from the group consisting of halogen and lower alkoxy. Especially preferred compounds are those in which R$^1$ and R$^2$ are both phenyl, optionally substituted by alkyl, halogen, or CF$_3$. Also among this group are compounds in which n is 1. Also preferred among this group are compounds in which X is hydrogen and those in which X is hydroxy. Further preferred among this group are compounds in which R$^3$ is hydrogen and those in which R³ is lower alkyl. Also preferred are such compounds where A-B is —CH₂—CH₂—.

Another preferred group of compounds are compounds of formula I in which R² is phenyl, optionally substituted by one or two substituents selected from the group consisting of halogen and lower alkoxy. Within this group, preferred compounds are those in which n is 1. Also preferred among this group are compounds in which X is hydrogen and those in which X is hydroxy. Further preferred among this group are compounds in which R³ is hydrogen and those in which R³ is lower alkyl. Also preferred are such compounds where A-B is —CH₂—CH₂—.

The present compounds of formula I and their pharmaceutically acceptable salts can be prepared by methods known in the art, for example, by processes described below, which processes comprise a) reacting a compound of formula

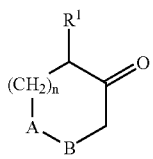

11 with a compound of formula

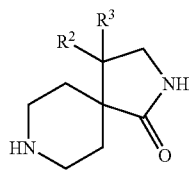

7 to produce a compound of formula

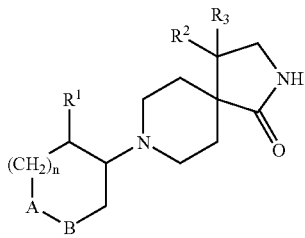

I where X = hydrogen, wherein the substituents are as defined above, or
b) reacting a compound of formula

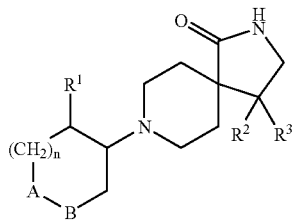

with a compound of formula

R¹Br 8 to produce a compound of formula

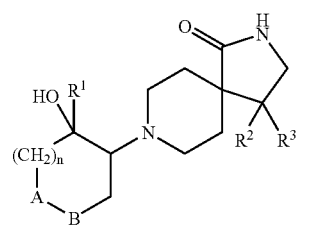

I where X = hydroxy wherein the substituents are as defined above, or
c) if desired, separating the obtained racemic forms into corresponding enantiomers, and if desired, converting the compounds obtained into pharmaceutically acceptable acid addition salts.

The compounds of formula I may be prepared in accordance with process variant a), b) or c) and with the following schemes 1, 2 and 3.

The following abbreviations have been used:
LDA=lithium diisopropylamide
TFA=trifluoroacetic acid
DCM=dichloromethane
THF=tetrahydrofuran
PMHS=polymethylhydrosiloxane
DMSO=dimethylsulfoxide The starting materials of formulas 2, 3, 8, 9 and 12 are known compounds or may be prepared by methods known to the skilled person.

Starting from an appropriately 1-protected-piperidine-4-alkylcarboxylate 2, treatment with LDA, followed by treatment with an appropriately substituted nitro alkene 3 results in formation of the nitro alkane 4. Reduction to the amino group facilitated by Raney-Ni and hydrogen, usually at 60 bar pressure and at 55° C. in EtOH as solvent results in the formation of 5. Subsequent cyclisation by heating in toluene under reflux affords the amide 6. Removal of the protecting group under standard conditions (TFA treatment in DCM for R=Boc; or hydrogenolysis with Pd/C in DCM, MeOH for R=Bn) affords the diazaspiropiperidines 7 (Scheme 1).

Scheme 1

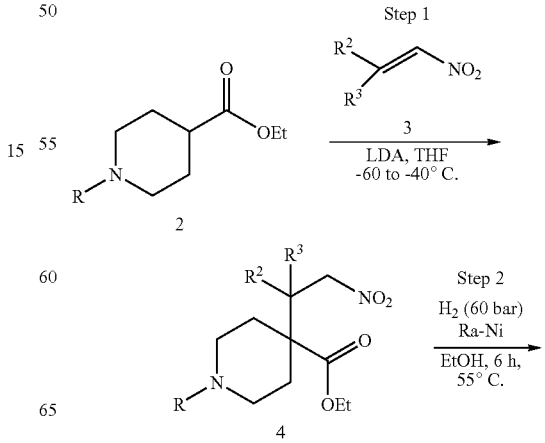

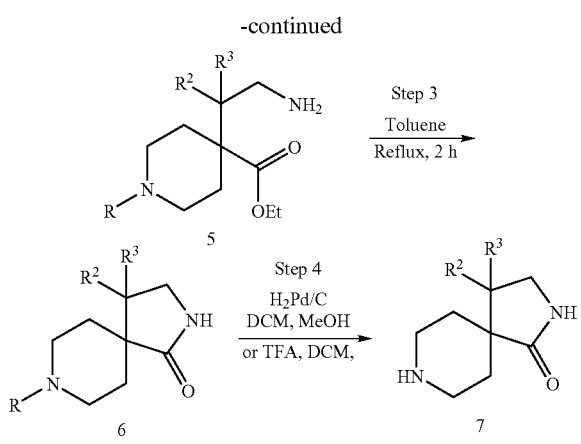

Further reaction of compounds of formula 7 with corresponding compounds of formula 11 (which can be prepared by reaction of the arylhalides of formula 8 with BuLi and subsequent reaction with an epoxide of formula 9 to give the alcohols of formula 10, which are oxidized to the corresponding ketones of formula 11 with Dess-Martin Periodinane) in the presence of Ti(OPr-i)$_4$ and NaBH(OAc)$_3$ to give compounds of formula I (Scheme 2). Alternatively, reaction of compounds of formulas 7 and 11 in the presence of Ti(OPr-i)$_4$ and NaBH(OAc)$_3$ (with or without the presence of PMHS) also gives products of formula I. An alternative strategy is one where overall reductive amination of the ketones of formula 11 with compounds of formula 12 in a Dean-Stark trap affords an intermediate enamine, which can be reduced in situ to the compound formula 13. Following steps 1–3 as described in Scheme 1 affords compounds of formula I.

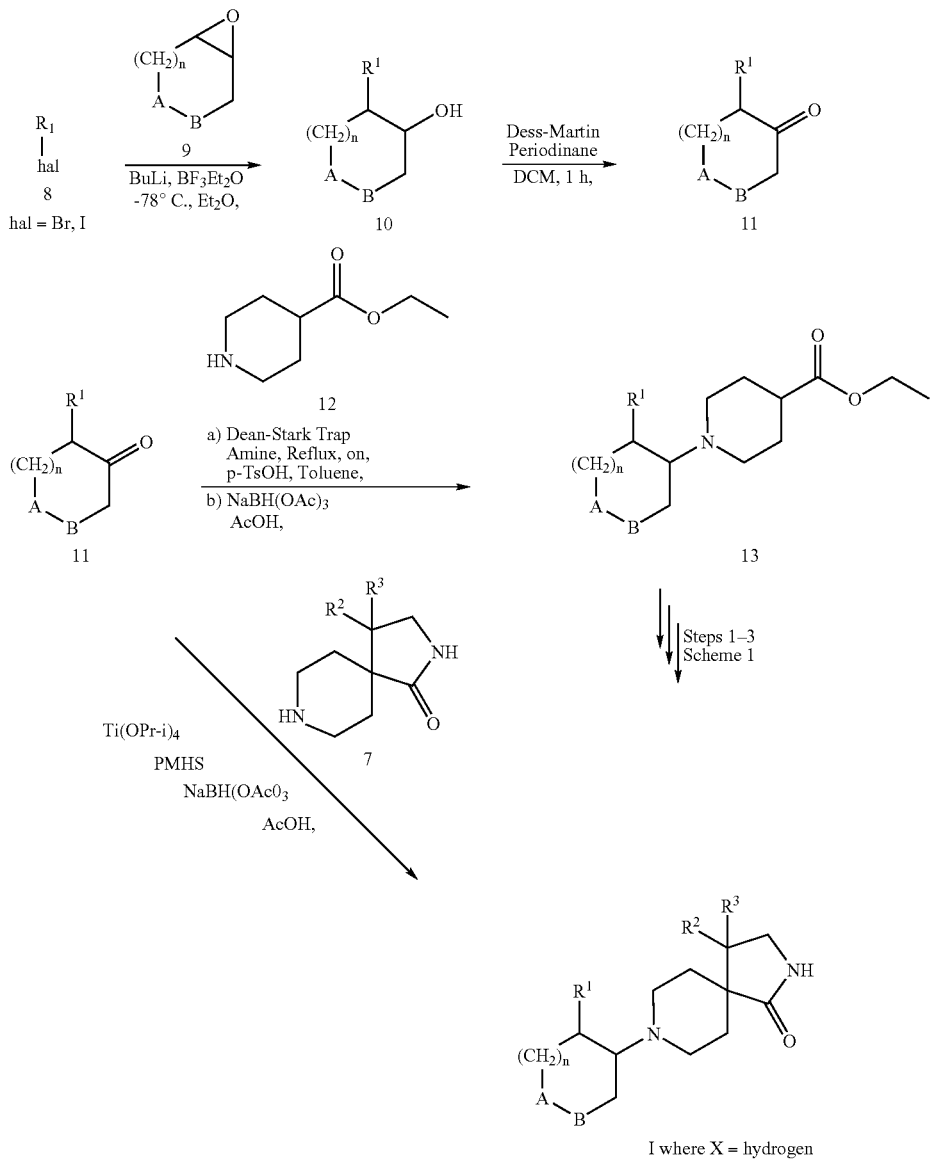

Compounds of formula I where X=OH are prepared by reacting a compound of formula 7 with an oxide of formula 9 in refluxing ethanol. The resulting β-aminoalcohol of formula 14 can then be oxidised to the ketone, preferably, with pyridine SO₃ complex in the presence of triethylamine in DMSO to give compounds of formula 15, which are then treated with aryl lithium reagents (formed by halogen-metal exchange) to provide access to the desired products of formula I (Scheme 3).

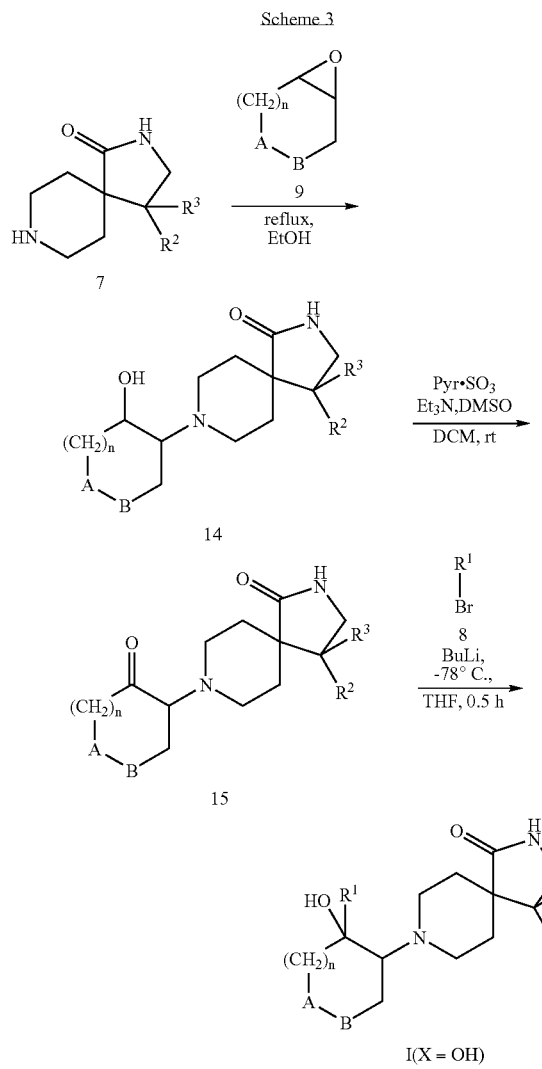

Scheme 3

All compounds of formulas I, 4, 5, 6, 7, 11, 10, 13, 14, 15 are usually formed during the sequence of reactions into an equal mixture of (R,R,S)-, (S,S,R)-, (R,R,R)- and (S,S,S)-enantiomers (racemic forms), following the procedures described below. They may separated into chiral non-racemic enantiomers by preparative iPLC using either a Chiralpak O D or AD column (5×50 cm) at room temperature using an ethanol:heptane mobile phase with UV detection at 220 nM.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention are good inhibitors of the glycine transporter I (GlyT-1).

The compounds were investigated in accordance with the test given hereinafter.

Solutions and Materials

DMEM complete medium: Nutrient mixture F-12 (Gibco Life-technologies), fetal bovine serum (FBS) 5%, (Gibco life technologies), Penicillin/Streptomycin1% (Gibco life technologies), Hygromycin 0.6 mg/ml (Gibco life technologies), Glutamine 1 mM Gibco life technologies).

Uptake buffer (UB): 150 mM NaCl, 10 mM Hepes-Tris, pH 7.4, 1 mM $CaCl_2$, 2.5 mM KCl, 2.5 mM $MgSO_4$, 10 mM (+) D-glucose.

Flp-in™-CHO (Invitrogen Cat n° R758–07) cells stably transfected with mGlyT1b cDNA.

Glycine Uptake Inhibition Assay (mGlyT-1b)

On day 1 mammalian cells, (Flp-in™-CHO), transfected with mGlyT-1b cDNA, were plated at the density of 40,000 cells/well in complete F-12 medium, without hygromycin in. 96-well culture plates. On day 2, the medium was aspirated and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of concentrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [³H]-glycine 60 nM (11–16 Ci/mmol) and 25 μM non-radioactive glycine. The plates were incubated with gentle shaking and the reaction was stopped by aspiration of the mixture and washing (three times) with ice-cold UB. The cells were lysed with scintillation liquid, shaken 3 hours and the radioactivity in the cells was counted using a scintillation counter.

The activity as inhibitor of the glycine transporter I (GlyT-1) is dependent on its racemic or enantiomeric form.

The preferred compounds show an $IC_{50}$ (nM) at GlyT-1<100.

| Example No. | $IC_{50}$ (nM) of some enantiomers |
|---|---|
| 1 | 61 |
| 2 | 105 |
| 6 | 48 |
| 7 | 36, 43 |
| 10 | 91 |
| 11 | 70 |
| 15 | 95, 77 |
| 16 | 69 |
| 17 | 73 |
| 29 | 91 |

The present invention also provides pharmaceutical compositions containing compounds of the invention and/or pharmaceutically acceptable salts thereof and a pharmaceutically acceptable carrier. Such pharmaceutical compositions can be in the form of tablets, coated tablets, dragees, hard and soft gelatin capsules, solutions, emulsions, or suspensions. The pharmaceutical compositions also can be in the form of suppositories or injectable solutions.

The pharmaceutical compositions of the invention, in addition to one or more compound of the invention, contain a pharmaceutically acceptable carrier. Suitable pharmaceutically acceptable carriers include pharmaceutically inert, inorganic or organic carriers for the production of pharmaceutical preparations. Lactose, corn starch or derivatives thereof, talc, stearic acids or its salts, and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions of the invention. Such process comprises bringing one or more compounds of the invention and/or pharmaceutically acceptable acid addition salts thereof and, if desired, one or more other therapeutically valuable substances into a galenical administration form together with one or more pharmaceutically acceptable carriers.

Compounds of the invention are inhibitors of the glycine transporter 1 (GlyT-1) and have good selectivity to glycine transporter 2 (GlyT-2) inhibitors. Thus, the compounds of the invention are useful for the treatment of diseases related to activation of NMDA receptors via Glyt-1 inhibition.

The invention further relates to the treatment of neurological and neuropsychiatric disorders with compounds of the invention. For example, the present invention provides methods for the treatment of illnesses such as psychoses, disfunction in memory and learning, schizophrenia, dementia and other diseases in which cognitive process are impaired, such as attention deficit disorders or Alzheimer's disease.

The most preferred indications in accordance with the present invention are those, which include disorders of the central nervous system, for example the treatment or prevention of schizophrenia, cognitive impairment and Alzheimer's disease. Thus, the invention provides a method for treating Alzheimer's disease which comprises administering to an individual a therapeutically effective amount of a compound of the invention, for example, a compound of formula I or a pharmaceutically active salt thereof. The invention also provides a method for treating schizophrenia which comprises administering to an individual a therapeutically effective amount of a compound of the invention, for example, a compound of formula I or a pharmaceutically active salt thereof. The invention further provides a method for improving cognition which comprises administering to an individual a therapeutically effective amount of a compound of the invention, for example, a compound of formula I or a pharmaceutically active salt thereof.

The compounds and compositions of the invention can be administered in a conventional manner, for example, orally, rectally, or parenterally. The pharmaceutical compositions of the invention can be administered orally, for example, in the form of tablets, coated tablets, dragees, hard and soft gelatin capsules, solutions, emulsions or suspensions. The pharmaceutical compositions also can be administered rectally, for example, in the form of suppositories or parenterally, for example, in the form of injectable solutions.

The dosage at which the compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it. All temperatures are given in degree Celsius.

Preparation of Building blocks 11 rac-2-(4-Fluoro-phenyl)-cyclohexanone rac-2-(4-Fluoro-phenyl)-cyclohexanol a) To a solution of 1-bromo-4-fluorobenzene (12.5 mL, 114 mmol) in diethylether (250 mL) at −78° C. was added BuLi (1.6 M, 68 mL, 109 mmol) under argon. After 5 min at this temperature, cyclohexenoxide (11.0 mL, 109 mmol) was added followed by the addition of borontrifluoride-diethyletherate (13.8 mL, 109 mmol) whereby the temperature increased to approx. −50° C. After 4 h at this temperature the reaction was quenched by the addition of ammonium chloride (saturated, 200 mL) and diluted with water (50 mL). The product was then extracted with diethylether (3×100 mL) and the combined organic extracts dried over sodium sulfate. Filtration and evaporation afforded the tide compound (11.9 g, 56%) as white crystals after trituration from hexane. MS: m/e=194.1 (M).

rac-2-(4-Fluoro-phenyl)-cyclohexanone bi) To a solution of rac-2-(4-fluoro-phenyl)-cyclohexanol (3.8 g, 20 mmol) in DCM (320 mL) was added Dess-Martin periodinane [1,1,1-tris(acetyloxy)-1,1-dihydro-1,2-benziodoxol-3-(1H)-one](10 g, 24 mmol) at room temperature and after 2 h the reaction mixture was washed with sodium hydrogen carbonate (10%, 150 mL). The organic phase was then separated and washed with sodium thiosulfite (10%, 150 mL) and then dried over sodium sulfate, filtered and evaporated. Purification by chromatography through silica gel, eluting with ethyl acetate:hexane (1:4) afforded the title compound (3.4 g, 89%) as white crystals. MS: m/e=192.1 (M).

rac-2-(4-Fluoro-phenyl)-cyclohexanone bii) Alternatively, to a solution of rac-2-(4-fluoro-phenyl)-cyclohexanol (7.5 g, 39 mmol) in dry DMSO (67 mL) was added triethylamine (27 mL, 190 mmol) under argon and the resulting mixture cooled to 0° C. and then a solution of sulfur trioxide pyridine complex (18.4 g, 116 mmol) in dry DMSO (98 mL) was added dropwise over 15 min. After 1 h, the mixture was diluted with water (200 mL) and the product extracted with DCM (2×100 mL). The combined organic extracts were then dried over sodium sulfate, followed by filtration and evaporation. Purification by filtration through silica gel, eluting with ethyl acetate:hexane (1:4) afforded the title compound (7.1 g, 95%) as white crystals. MS: m/e=192.1 (M).

rac-2-p-Tolyl-cyclohexanone rac-2-p-Tolyl-cyclohexanol
a) To a solution of p-tolylbromide (17.1 g, 100 mmol) in dry THF (100 mL) was added magnesium (2.43 g, 100 mmol) and then the resulting mixture was cooled to −20° C. and (CuBr-dimethylsulfide complex (2.0 g, 10 mmol) was added and the mixture stirred at −20° C. for 10 min. Then a solution of cyclohexene oxide (10 mL, 100 mmol) in dry THF (10 mL) was added dropwise and the reaction warmed to 0° C. at which point an exothermic reaction initiates. With ice-bath cooling the temperature can be maintained below 25° C. The reaction mixture was then stirred at 0–5° C. for an additional 2 h, then quenched with ammonium chloride solution (saturated, 30 mL) and the product extracted with tert-butyl methyl ether. The combined organic extracts were then washed with water, dried over sodium sulfate, filtered and evaporated. Recrystallisation from hexane afforded the title compound (9.9 g, 52%) as white crystals. MS: m/e=190.1 (M).

rac-2-p-Tolyl-cyclohexanone
b) As described for building block 11 step bi, rac-2-p-tolyl-cyclohexanol (4.86 g, 26 mmol) was converted to the tide compound (4.68 g, 97%) which was obtained as white crystals. MS: m/e=188.1 (M).

rac-2-(4-Trifluoromethyl-phenyl)-cyclohexanone rac-2-(4-Trifluoromethyl-phenyl)-cyclohexanol
a) As described for building block 11 step a, 4-bromobenzotrifluoride (10.0 g, 44 mmol) was converted to the title compound (5.64 g, 52%) which was obtained as a white solid. MS: m/e=244.1 (M).

rac-2-(4-Trifluoromethyl-phenyl)-cyclohexanone
b) As described for building block 11 step bi, rac-2-(4-trifluoromethyl-phenyl)-cyclohexanol (5.5 g, 23 mmol) was converted to the title compound (5.26 g, 96%) which was obtained as a white solid. MS: m/e=242.1 (M).

rac-2-(4-Trifluoromethoxy-phenyl)-cyclohexanone rac-2-(4-Trifluoromethoxy-phenyl)-cyclohexanol
a) As described for building block 11 step a,1-bromo-4-(trifluoromethoxy)benzene (10.3 g, 43 mmol) was converted to the title compound (6.7 g, 60%) which was obtained as a white solid. MS: m/e=260.1 (M).

rac-2-(4-Trifluoromethoxy-phenyl)-cyclohexanone
b) As described for building block 11 step bi, rac-2-(4-trifluoromethoxy-phenyl)-cyclohexanol (6.6 g, 25 mmol) was converted to the title compound (5.36 g, 82%) which was obtained as a white solid. MS: m/e=258.2 (M).

rac-2-(3-Fluoro-phenyl)-cyclohexanone rac-2-(3-Fluoro-phenyl)-cyclohexanol
a) As described for building block 11 step a, 1-bromo-3-fluorobenzene (10.0 g, 57 mmol) was converted to the title compound (5.1 g, 46%) which was obtained as a white solid. MS: m/e=194.1 (M).

rac-2-(3-Fluoro-phenyl)-cyclohexanone
As described for building block 11 step bi, rac-2-(3-fluoro-phenyl)-cyclohexanol (5.0 g, 26 mmol) was converted to the title compound (3.9 g, 80%) which was obtained as a white solid. MS: m/e=192.1 (M).

rac-2-(3-Trifluoromethyl-phenyl)-cyclohexanone rac-2-(3-Trifluoromethyl-phenyl)-cyclohexanol
a) As described for building block 11 step a, 3-bromobenzotrifluoride (10.0 g, 44 mmol) was converted to the title compound (4.87 g, 45%) which was obtained as a white solid. MS: m/e=244.1 (M).

rac-2-(3-Trifluoromethyl-phenyl)-cyclohexanone
b) As described for building block 11 step bi, rac-2-(3-trifluoromethyl-phenyl)-cyclohexanol (4.7 g, 19 mmol) was converted to the title compound (4.34 g, 93%) which was obtained as a light yellow oil. MS: m/e=242.1 (M).

rac-2-(3-Fluoro-4-methyl-phenyl)-cyclohexanone rac-2-(3-Fluoro-4-methyl-phenyl)-cyclohexanol
a) As described for building block 11 step a, 4-bromo-2-fluorotoluene (10.0 g, 53 mmol) was converted to the title compound (6.33 g, 58%) which was obtained as a white solid. MS: m/e=208.3 (M).

rac-2-(3-Fluoro-4-methyl-phenyl)-cyclohexanone
b) As described for building block 11 step bi, rac-2-(3-Fluoro-4-methyl-phenyl)-cyclohexanol (6.2 g, 30 mmol) was converted to the title compound (5.53 g, 91%) which was obtained as a white solid. MS: m/e=206.1 (M).

rac-2-(4-Methyl-3-trifluoromethyl-phenyl)-cyclohexanone rac-2-(4-Methyl-3-trifluoromethyl-phenyl)-cyclohexanol
a) As described for building block 11 step a, 4-methyl-3-(trifluoromethyl)bromobenzene (4.2 g, 18 mmol) was converted to the title compound (1.95 g, 43%) which was obtained as a white solid. MS: m/e=258.2 (M).

rac-2-(4-Methyl-3-trifluoromethyl-phenyl)-cyclohexanone
b) As described for building block 11 step bi, rac-2-(4-methyl-3-trifluoromethyl-phenyl)-cyclohexanol (1.91 g, 7 mmol) was converted to the title compound (1.8 g, 95%) which was obtained as a white solid. MS: m/e=256.1 (M).

rac-2-(4-Fluoro-3-methyl-phenyl)-cyclohexanone rac-2-(4-Fluoro-3-methyl-phenyl)-cyclohexanol
a) As described for building block 11 step a, 5-bromo-2-fluorotoluene (10.0 g, 53 mmol) was converted to the title compound (5.47 g, 50%) which was obtained as a white solid. MS: m/e=208.2 (M).

rac-2-(4-Fluoro-3-methyl-phenyl)-cyclohexanone
b) As described for building block 11 step bi, rac-2-(4-fluoro-3-methyl-phenyl)-cyclohexanol (5.4 g, 26 mmol) was converted to the title compound (14.7 g, 88%) which was obtained as a light yellow oil. MS: m/e=206.1 (M).

rac-2-(4-Chloro-3-trifluoromethyl-phenyl)-cyclohexanone rac-2-(4-Chloro-3-trifluoromethyl-phenyl)-cyclohexanol
a) As described for building block 11 step a, 5-bromo-2-chlorobenzotrifluoride (8.32 g, 30 mmol) was converted to the title compound (4.4 g, 52%) which was obtained as a white solid. MS: m/e=278.1 (M).

rac-2-(4-Chloro-3-trifluoromethyl-phenyl)-cyclohexanone b) As described for building block 11 step bi, rac-2-(4-chloro-3-trifluoromethyl-phenyl)-cyclohexanol (4.3 g, 15 mmol) was converted to the title compound (4.13 g, 97%) which was obtained as a white solid. MS: m/e=276.1 (M).

Preparation of Building blocks 7 rac-4-Phenyl-2,8-diaza-spiro[4.5]decan-1-one rac-1-Benzyl-4-(2-nitro-1-phenyl-ethyl)-piperidine-4-carboxylic acid ethyl ester a) An LDA (14 mmol) solution was prepared by treating diisopropylamine (1.37 g, 14 mmol) with BuLi (1.6 M, 8.5 mL, 14 mmol) at −78° C. in dry THF (10 mL) under argon and allowing to warm up to −20° C. This solution was then cooled to −60° C. added to a solution of 1-benzyl-piperidine-4-ethyl carboxylate (3.05 g, 12 mmol) in THF (8 mL) at −60° C. and allowed to warm up to −40° C. over 1 h whereupon a solution of trans-beta-nitrostyrene (1.93 g, 13 mmol) in THF (8 mL) was added dropwise. The reaction mixture was allowed to warm up to room temperature over 1 h and then quenched with ammonium chloride (saturated, 40 mL) and the product extracted with ethyl acetate (2×40 mL). The combined organic extracts were then washed with brine, dried over sodium sulfate, filtered and evaporated. Purification by chromatography on silica gel eluting with DCM:MeOH (9:1) afforded the title compound (4.1 g, 84%) as a light yellow gum. MS: m/e=397.4 (M+H).

rac-4-(2-Amino-1-phenyl-ethyl)-1-benzyl-piperidine-4-carboxylic acid ethyl ester b) A solution of rac-1-benzyl-4-(2-nitro-1-phenyl-ethyl)-piperidine-4-carboxylic acid ethyl ester (3.18 g, 8 mmol) in dry EtOH (240 mL) was hydrogenated in the presence of Ra—Ni (3 g) at 60 bar at 55° C. for 3 h. After cooling and decompression of the reaction vessel, the mixture was filtered over celite and the filtrate evaporated to leave the title compound (2.9 g, 99%) as a clear oil. MS: m/e=367.4 (M+H).

rac-8-Benzyl-4-phenyl-2,8-diaza-spiro[4.5]decan-1-one c) A solution of rac-4-(2-amino-1-phenyl-ethyl)-1-benzyl-piperidine-4-carboxylic acid ethyl ester (2.9 g, 8 mmol) in toluene (30 mL) was heated under reflux for 4 h. After cooling to room temperature and evaporation the mixture was purified by chromatography on silica gel eluting with DCM:MeOH:NH$_4$OH (95:4.5:0.5) to afford the title compound (1.47 g, 58%) as a white solid. MS: m/e=321.4 (M+H).

rac-4-Phenyl-2,8-diaza-spiro[4.5]decan-1-one d) A suspension of rac-8-benzyl-4-phenyl-2,8-diaza-spiro[4.5]decan-1-one (28.8 g, 90 mmol) in MEOH:DCM (4:1, 500 mL) was hydrogenated in the presence of Pd (10% on C, 14 g, 132 mmol) at 2 bar for 48 h at room temperature. After filtration over celite, the reaction mixture was evaporated and the residue dissolved in NaOH (2 N, 200 mL). The product was extracted with DCM (3×150 mL) and the combined organic extracts dried over sodium sulfate. Filtration and evaporation afforded the title compound (13.1 g, 63%) as a white solid after trituration from diethylether. MS: m/e=231.4 (M+H).

Scheme 1, Step 1: F-derivative from Boc protecting group rac-4-(4-Fluoro-phenyl)-2,8-diaza-spiro[4.5]decan-1-one Piperidine-1,4-dicarboxylic acid 1-tert-butyl ester 4-ethyl ester a) To a solution of ethyl isonipecotate (20 g, 127 mmol) in dioxane:water (1:1, 120 mL) was added triethylamine (12.87 g, 127 mmol) at 0° C. followed by di-tert-butyl dicarbonate (35.2 g, 161 mmol) and the resulting mixture maintained at this temperature for 2 h. The product was then extracted with ethyl acetate (3×100 mL) and the combined organic extracts washed with HCl (1 N, 100 mL), brine (100 mL), dried over sodium sulfate, filtered and evaporated. Purification by Kugelrohr distillation afforded the title compound (29.0 g, 89%) as a colourless liquid, bp 140° C. at 0.13 mbar. MS: m/e=275.2 (M+NH$_4$).

rac-4-[1-(4-Fluoro-phenyl)-2-nitro-ethyl]-piperidine-1,4-dicarboxylic acid 1-tert-butyl ester 4-ethyl ester b) An LDA solution was prepared by treating diisopropylamine (6.98 g, 69 mmol) with BuLi (1.6 M, 41.3 mL, 66 mmol) at −78° C. in dry THF (45 mL) under argon and allowing to warm up to −20° C. This solution was then cooled to −60° C. added to a solution of piperidine-1,4-dicarboxylic acid 1-tert-butyl ester 4-ethyl ester (15.44 g, 60 mmol) in dry THF (45 mL) at −60° C. and allowed to warm up to −40° C. over 1 h whereupon a solution of 4-fluoro-trans-beta-nitrostyrene (10.02 g, 60 mmol) in dry THF (40 mL) was added dropwise. The reaction mixture was allowed to warm up to room temperature over 1 h and then quenched with ammonium chloride (saturated, 250 mL) and the product extracted with diethylether (3×100 mL). The combined organic extracts were then washed with brine, dried over sodium sulfate, filtered and evaporated to afford the title compound (26.7 g, 99%) as a light yellow gum. MS: m/e=442.4 (M+NH$_4$).

rac-4-(2-Amino-1-phenyl-ethyl)-1-tert-butyl-piperidine-1,4-dicarboxylic acid ethyl ester c) A solution of rac-4-[1-(4-fluoro-phenyl)-2-nitro-ethyl]-piperidine-1,4-dicarboxylic acid 1-tert-butyl ester 4-ethyl ester (26.6 g, 60 mmol) in dry EtOH (600 mL) was hydrogenated in the presence of Ra—Ni (25 g) at 50 bar at 50° C. for 20 h. After cooling and decompression of the reaction vessel, the mixture was filtered over celite and the filtrate evaporated to leave the title compound (23.4 g, 99%) as a clear oil which was used directly in the next step.

rac-4-(4-Fluoro-phenyl)-1-oxo-2,8-diaza-spiro[4.5]decane-8-carboxylic acid tert-butyl ester d) A solution of 4-(2-amino-1-phenyl-ethyl)-1-tert-butyl-piperidine-1,4-dicarboxylic acid ethyl ester (23.4 g, 60 mmol) in toluene (200 mL) was heated under reflux for 18 h. After cooling to room temperature, evaporation afforded the title compound (17.17 g, 83%) as a white solid after trituration from hot pentane. MS: m/e=349.3 (M+H).

rac-4-(4-Fluoro-phenyl)-2,8-diaza-spiro[4.5]decan-1-one e) A solution of 4-(4-fluoro-phenyl)-1-oxo-2,8-diaza-spiro[4.5]decane-8-carboxylic acid tert-butyl ester (46.0 g, 132 mmol) in DCM (260 mL) containing TFA (150 mL, 1.32 mol) was stirred vigorously at 0° C. for 15 min. The reaction mixture was then poured into NaOH (3 N, 200 mL) and the product extracted with DCM (3×100 mL). The combined organic extracts were then washed with water (100 mL) and brine (100 mL) and then dried over sodium sulfate. Filtration and evaporation afforded the title compound (22.14 g, 68%) as a white solid after trituration from ethyl acetate. MS: m/e=249.2 (M+H).

EXAMPLE 1 cis-rac-4-Phenyl-8-(2-phenyl-cyclohexyl)-2,8-diaza-spiro[4.5]decan-1-one cis-rac-1-(2-Phenyl-cyclohexyl)-piperidine-4-carboxylic acid ethyl ester
a) A solution of ethyl isonipecotate (3.7 g, 24 mmol), 2-phenylcyclohexanone (5.0 g, 29 mmol) in toluene (50 mL) containing para-toluenesulfonic acid (446 mg, 2 mmol) was heated under reflux with a Dean-Stark trap for 13 h. After cooling to room temperature the mixture was evaporated to leave approximately 15 mL of solution and then diluted with 1,2-dichloroethane (120 mL) and then acetic acid (0.95 mL) was added followed by the portionwise addition of sodium triacetoxyborohydride (7.3 g, 33 mmol). After 3.5 h the mixture was quenched with NaOH (3 N, 50 mL), diluted with water (50 mL) and the organic layer separated. The organic layer was then dried and evaporated to leave a residue which was purified by silica gel chromatography eluting with heptane:ethyl acetate (9:1) to (4:1) to (3:2) to afford the title compound as a light yellow oil (5.5 g, 75%). MS: m/e=316.2 (M+H).

cis-rac 4-(2-Nitro-1-phenyl-ethyl)-1-(2-phenyl-cyclohexyl)-piperidine-4-carboxylic acid ethyl ester
b) As described for building block 7 step a, 1-(2-phenyl-cyclohexyl)-piperidine-4-carboxylic acid ethyl ester (1.0 g, 3 mmol) was converted to the title compound (1.1 g, 73%) which was obtained as an off-white solid. MS: m/e=465.4 (M+H).

cis-rac-4-Phenyl-8-(2-phenyl-cyclohexyl)-2,8-diaza-spiro[4.5]decan-1-one
c) As described for building block 7 step b, 4-(2-nitro-1-phenyl-ethyl)-1-(2-phenyl-cyclohexyl)-piperidine-4-carboxylic acid ethyl ester (1.0 g, 2 mmol) was converted to the amino compound (810 mg, 87%) which was obtained as a light yellow oil and used directly in the next step. MS: m/e=435.4 (M+H).

d) As described for example building block 7 step c, the amino compound (810 mg, 2 mmol) was converted to the title compound (607 mg, 93%) which was obtained as a white solid. MS: m/e=389.4 (M+H).

EXAMPLE 2

Cis-rac-4-Phenyl-8-(2-p-tolyl-cyclohexyl)-2,8-diaza-spiro[4.5]decan-1-one

A mixture of rac-2-p-tolyl-cyclohexanone (410 mg, 2 mmol), rac-4-phenyl-2,8-diaza-spiro[4.5]decan-1-one (502 mg, 2 mmol) and titanium(IV) isopropoxide (810 uL, 3 mmol) were stirred at rt for 3 h. The mixture was then diluted with THF (5 mL) and then a solution of polymethylhydroxysiloxane (261 mg, 4 mmol) in THF (5 mL) was added and the resulting solution stirred at rt overnight. To this solution Na(CN)BH$_3$ (245 mg) was added and the resulting mixture stirred at rt for 3 h. Then NaOH (3M, 10 mL) was added and the mixture stirred for 1 h. The resulting precipitate was then filtered off over celite and the filtrate was washed with brine, dried and evaporated to leave a light yellow foam. Purification by chromatography on silica gel eluting with DCM:MeOH:NH$_4$OH (25%) (98:2:0.1 to 95:4.5:0.5) afforded the title compound (250 mg, 29%) which was obtained as a white solid. MS: m/e=403.6 (M+H).

EXAMPLE 3 cis-rac-4-(4-Fluoro-phenyl)-8-(2-p-tolyl-cyclohexyl)-2,8-diaza-spiro[4.5]decan-1-one cis-rac-1-(2-p-Tolyl-cyclohexyl)-piperidine-4-carboxylic acid ethyl ester
a) As described for example 1a, rac-2-p-tolyl-cyclohexanone (4.2 g, 22 mmol) was converted to the title compound (3.7 g, 48%) which was obtained as a light yellow oil. MS: m/e=330.4 (M+H).

cis-rac-4-[1-(4-Fluoro-phenyl)-2-nitro-ethyl]-1-(2-p-tolyl-cyclohexyl)-piperidine-4-carboxylic acid ethyl ester
b) As described for example 1b, cis-rac-1-(2-p-tolyl-cyclohexyl)-piperidine-4-carboxylic acid ethyl ester (700 mg, 2 mmol) was converted to the title compound (880 mg, 83%) which was obtained as a yellow gum MS: m/e=497.3 (M+H).

cis-rac 4-(4-Fluoro-phenyl)-8-(2-p-tolyl-cyclohexyl)-2,8-diaza-spiro[4.5]decan-1-one
c) As described for example 1c, cis-rac-4-[1-(4-fluoro-phenyl)-2-nitro-ethyl]-1-(2-p-tolyl-cyclohexyl)-piperidine-4-carboxylic acid ethyl ester (880 mg, 2 mmol) was converted to the amino compound (670 mg, 81%) which was obtained as a yellow gum and used directly in the next step. MS: m/e=467.3 (M+H).

d) As described for example 1d, the amino compound (665 mg, 1 mmol) was converted to the title compound (130 mg, 22%) which was obtained as a light yellow solid. MS: m/e=421.2 (M+H).

EXAMPLE 4 cis-rac-4-(3,4-Dichloro-phenyl)-8-(2-p-tolyl-cyclohexyl)-2,8-diaza-spiro[4.5]decan-1-one cis-rac-4-[1-(3,4-Dichloro-phenyl)-2-nitro-ethyl]-1-(2-p-tolyl-cyclohexyl)-piperidine-4-carboxylic acid ethyl ester
a) As described for example 1b, rac-1-(2-p-tolyl-cyclohexyl)-piperidine-4-carboxylic acid ethyl ester (700 mg, 2 mmol) was converted to the title compound (772 mg, 66%) which was obtained as a yellow solid. MS: m/e=547.2 (M).

b) As described for example 1c, cis-rac-4-[1-(3,4-dichloro-phenyl)-2-nitro-ethyl]-1-(2-p-tolyl-cyclohexyl)-piperidine-4-carboxylic acid ethyl ester (772 mg, 1 mmol) was converted to the title compound (43 mg, 6%) which was obtained as a yellow gum. MS: m/e=471.3 (M).

EXAMPLE 5 cis-rac-4-(4-Methoxy-phenyl)-8-(2-p-tolyl-cyclohexyl)-2,8-diaza-spiro[4.5]decan-1-one cis-rac-4-[1-(4-Methoxy-phenyl)-2-nitro-ethyl]-1-(2-p-tolyl-cyclohexyl)-piperidine-4-carboxylic acid ethyl ester
a) As described for example 1b, rac-1-(2-p-tolyl-cyclohexyl)-piperidine-4-carboxylic acid ethyl ester (700 mg, 2 mmol) was converted to the title compound (620 mg, 57%) which was obtained as a yellow gum. MS: m/e=509.4 (M+H).

cis-rac-4-(4-Methoxy-phenyl)-8-(2-p-tolyl-cyclohexyl)-2,8-diaza-spiro[4.5]decan-1-one.

b) As described for example 1c, cis-rac-4-[1-(4-methoxy-phenyl)-2-nitro-ethyl]-1-(2-p-tolyl-cyclohexyl)-piperidine-4-carboxylic acid ethyl ester (620 mg, 1 mmol) was converted to the title compound (410 mg, 70%) which was obtained as a yellow gum. MS: m/e=433.5 (M+H).

EXAMPLE 6 cis-rac-8-[2-(4-Fluoro-phenyl)-cyclohexyl]-4-phenyl-2,8-diaza-spiro[4.5]decan-1-one As described for example 2, rac-2-(4-fluoro-phenyl)-cyclohexanone (417 mg, 2 mmol) was converted to the title compound (150 mg, 17%) (using 4-phenyl-2,8-diaza-spiro[4.5]decan-1-one instead of 4-(4-fluoro-phenyl)-2,8-diaza-spiro[4.5]decan-1-one) which was obtained as a white solid. MS: m/e=407.5 (M+H).

Alternatively cis-rac-8-[2-(4-Fluoro-phenyl)-cyclohexyl]-4-phenyl-2,8-diaza-spiro[4.5]decan-1-one cis-rac-1-[2-(4-Fluoro-phenyl)-cyclohexyl]-4-(2-nitro-1-phenyl-ethyl)-piperidine-4-carboxylic acid ethyl ester a) As described for example 1b, cis-rac-1-[2-(4-fluoro-phenyl)-cyclohexyl]-piperidine-4-carboxylic acid ethyl ester (800 mg, 2.4 mmol) was converted to the title compound (677 mg, 59%) which was obtained as a light yellow gum. MS: m/e=483.3 (M).

cis-rac-8-[2-(4-Fluoro-phenyl)-cyclohexyl]-4-phenyl-2,8-diaza-spiro[4.5]decan-1-one b) As described for example 1c, 1-[2-(4-fluoro-phenyl)-cyclohexyl]-4-(2-nitro-1-phenyl-ethyl)-piperidine-4-carboxylic acid ethyl ester (627 mg, 1.3 mmol) was converted to the amino compound (497 mg, 85%) which was obtained as a light yellow oil and used directly in the next step. MS: m/e=453.6 (M).

c) As described for example 1d, the amino compound (497 mg, 1.1 mmol) was converted to the title compound (197 mg, 4 4%) which was obtained as an off-white solid. MS: m/e 407.3 (M+H).

EXAMPLE 7 cis-rac-4-(4-Fluoro-phenyl)-8-[2-(4-fluoro-phenyl)-cyclohexyl]-2,8-diaza-spiro[4.5]decan-1-one cis-rac-1-[2-(4-Fluoro-phenyl)-cyclohexyl]-piperidine-4-carboxylic acid ethyl ester a) As described for example 1a, rac-2-(4-fluoro-phenyl)-cyclohexanone (7.0 g, 36 mmol) was converted to the title compound (4.5 g, 38%) which was obtained as a light yellow oil. MS: m/e=334.3 (M+H).

cis-rac-1-[2-(4-Fluoro-phenyl)-cyclohexyl]-4-[1-(4-fluoro-phenyl)-2-nitro-ethyl]-piperidine-4-carboxylic acid ethyl ester b) As described for example 1b, cis-rac-1-[2-(4-fluoro-phenyl)-cyclohexyl]-piperidine-4-carboxylic acid ethyl ester (1.0 g, 3 mmol) (using 4-fluoro-trans-beta-nitrostyrene instead of trans-beta-nitrostyrene) was converted to the title compound (1.2 g, 77%) which was obtained as a white solid. MS: m/e=501.4 (M+H).

cis-rac-4-(4-Fluoro-phenyl)-8-[2-(4-fluoro-phenyl)-cyclohexyl]-2,8-diaza-spiro[4.5]decan-1-one c) As described for example 1c, cis-rac-1-[2-(4-fluoro-phenyl)-cyclohexyl]-4-[1-(4-fluoro-phenyl)-2-nitro-ethyl]-piperidine-4-carboxylic acid ethyl ester (1.1 g, 2 mmol) was converted to the amino compound (1.0 g, 99%) which was obtained as a light yellow oil and used directly in the next step. MS: m/e=471.3 (M+H).

d) As described for example 1d, the amino compound (1.05 g, 2 mmol) was converted to the title compound (670 mg, 71%) which was obtained as a white solid. MS: m/e=425.2 (M+H).

cis-rac-4-(4-Fluoro-phenyl)-8; [2-(4-fluoro-phenyl)-cyclohexyl]-2,8-diaza-spiro[4.5]decan-1-one e) Alternatively a mixture of rac-2-(4-fluoro-phenyl)-cyclohexanone (775 mg, 3 mmol), rac-4-(4-fluoro-phenyl)-2,8-diaza-spiro[4.5]decan-1-one (500 mg, 3 mmol) and titanium (IV) isopropoxide (887 uL, 3 mmol) were stirred at 60° C. overnight. The resulting solution was then cooled to room temperature and Na(CN)BH$_3$ (245 mg, 4 mmol) was added and the resulting mixture stirred at 50° C. for 3 h. Then NaOH (6M, 15 mL) was added and the mixture stirred for 1 h. The resulting mixture was then filtered off over celite and the filtrate was washed with brine, dried and evaporated to leave a light yellow foam. Purification by chromatography on silica gel eluting with DCM:MeOH:NH$_4$OH (25%) (98:2:0.1 to 95:4.5:0.5) afforded the title compound (212 mg, 20%) which was obtained as a white solid. MS: m/e=425.2 (M+H).

cis-rac-4-(4-Fluoro-phenyl)-8-[2-(4-fluoro-phenyl)-cyclohexyl]-2,8-diaza-spiro[4.5]decan-1-one f) Alternatively as described for example 2, rac-2-(4-fluoro-phenyl)-cyclohexanone (500 mg, 3 mmol) was converted to the title compound (219 mg, 20%) which was obtained as a white solid. MS: m/e=425.2 (M+H).

EXAMPLE 8 cis-rac-4-(3,4-Dichloro-phenyl)-8-[2-(4-fluoro-phenyl)-cyclohexyl]-2,8-diaza-spiro[4.5]decan-1-one cis-rac-4-[1-(3,4-Dichloro-phenyl)-2-nitro-ethyl]-1-[2-(4-fluoro-phenyl)-cyclohexyl]-piperidine-4-carboxylic acid ethyl ester a) As described for example 1b, cis-rac-1-[2-(4-fluoro-phenyl)-cyclohexyl]-piperidine-4-carboxylic acid ethyl ester (800 mg, 2.4 mmol) (using 3,4-dichloro-omega-nitrostyrene instead of trans-beta-nitrostyrene) was converted to the title compound (779 mg, 59%) which was obtained as a light yellow foam. MS: m/e=551.3 (M).

cis-rac-4-(3,4-Dichloro-phenyl)-8-[2-(4-fluoro-phenyl)-cyclohexyl]-2,8-diaza-spiro[4.5]decan-1-one b) As described for example 1c, cis-rac-4-[1-(3,4-dichloro-phenyl)-2-nitro-ethyl]-1-[2-(4-fluoro-phenyl)-cyclohexyl]-piperidine-4-carboxylic acid ethyl ester (729 mg, 1.3 mmol) was converted to the amino compound (646 mg, 93%) which was obtained as a light yellow oil and used directly in the next step.

c) As described for example 1d, the amino compound (646 mg, 1.2 mmol) was converted to the title compound (270 mg, 46%) which was obtained as an off-white solid. MS: m/e=475.2 (M).

EXAMPLE 9 cis-rac-8-[2-(4-Fluoro-phenyl)-cyclohexyl]-4-(4-methoxy-phenyl)-2,8-diaza-spiro[4.5]decan-1-one cis-rac-1-[2-(4-Fluoro-phenyl)-cyclohexyl]-4-[1-(4-methoxy-phenyl)-2-nitro-ethyl]-piperidine-4-carboxylic acid ethyl ester a) As described for example 1b, cis-rac-1-[2-(4-fluoro-phenyl)-cyclohexyl]-piperidine-4-carboxylic acid ethyl ester (800 mg, 2.4 mmol) (using 4-methoxy-beta-nitrostyrene instead of trans-beta-nitrostyrene) was converted to the title compound (642 mg) 52%) which was obtained as a light yellow foam. MS: m/e=513.4 (M+H).

cis-rac-4-(3,4-Dichloro-phenyl)-8-[2-(4-fluoro-phenyl)-cyclohexyl]-2,8-diaza-spiro[4.5]decan-1-one b) As described for example 1c, cis-rac-1-[2-(4-fluoro-phenyl)-cyclohexyl]-4-[1-(4-methoxy-phenyl)-2-nitro-methyl]-piperidine-4-carboxylic acid ethyl ester (601 mg, 1.2 mmol) was converted to the amino compound (523 mg, 92%) which was obtained as a light yellow oil and used directly in the next step. MS: m/e=483.5 (M+H).

c) As described for example 1d, the amino compound (523 mg, 1.1 mmol) was converted to the title compound (216 mg, 46%) which was obtained as a white foam. MS: m/e=437.3 (M+H).

EXAMPLE 10 cis-rac-4-(4-Fluoro-phenyl)-8-[2-(4-trifluoromethyl-phenyl)-cyclohexyl]-2,8-diaza-spiro[4.5]decan-1-one cis-rac-1-[2-(4-Trifluoromethyl-phenyl)-cyclohexyl]-piperidine-4-carboxylic acid ethyl ester a) As described for example 1a, rac-2-(4-trifluoromethyl-phenyl)-cyclohexanone (5.0 g, 21 mmol) was converted to the tide compound (2.7 g, 34%) which was obtained as a light yellow oil. MS: m/e=384.2 (M+H).

cis-rac-4-[1-(4-Fluoro-phenyl)-2-nitro-ethyl]-1-[2-(4-trifluoromethyl-phenyl)-cyclohexyl]-piperidine-4-carboxylic acid ethyl ester b) As described for example 1b, 1-[2-(4-trifluoromethyl-phenyl)-cyclohexyl]-piperidine-4-carboxylic acid ethyl ester (1.0 g, 3 mmol) was converted to the title compound (610 mg, 43%) which was obtained as a light yellow oil. MS: m/e=551.3 (M+H).

cis-rac-4-(4-Fluoro-phenyl)-8-[2-(4-trifluoromethyl-phenyl)-cyclohexyl]-2,8-diaza-spiro[4.5]decan-1-one c) As described for example 1c, 4-[1-(4-fluoro-phenyl)-2-nitro-ethyl]-1-[2-(4-trifluoromethyl-phenyl)-cyclohexyl]-piperidine-4-carboxylic acid ethyl ester (610 mg, 1 mmol) was converted to the amino compound (345 mg, 60%) which was obtained as a light yellow oil and used directly in the next step. MS: m/e=521.4 (M+H).

d) As described for example 1d, the amino compound (345 mg, 1 mmol) was converted to the title compound (268 mg, 85%) which was obtained as a white solid. MS: m/e=475.4 (M+H).

Preparation of Building blocks 15 rac-8-(2-Oxo-cyclohexyl)-4-phenyl-2,8-diaza-spiro[4.5]decan-1-one rac-8-(2-Hydroxy-cyclohexyl)-4-phenyl-2,8-diaza-spiro[4.5]decan-1-one a) A suspension of rac-4-phenyl-2,8-diaza-spiro[4.5]decan-1-one (13.10 g, 56.9 mmol) and 7-oxa-bicyclo[4.1.0]heptane (5.58 g, 56.9 mmol) in ethanol (250 mL) was heated under reflux for 3 days. After cooling to room temperature the mixture was filtered and the filtrate evaporated to afford the title compound (18.14 g, 97%) which was obtained as off-white solid. MS: m/e=329.3 (M+H).

rac-8-(2-Oxo-cyclohexyl)-4-phenyl-2,8-diaza-spiro[4.5]decan-1-one b) As described for building block 11 step bi, 8-(2-hydroxy-cyclohexyl)-4-phenyl-2,8-diaza-spiro[4.5]decan-1-one (18.10 g, 55.0 mmol) was converted to the title compound (15.26 g, 76%) which was obtained as a light yellow solid after trituration from hot diethylether. MS: m/e=327.2 (M+H).

rac-4-(4-Fluoro-phenyl)-8-(2-oxo-cyclohexyl)-2,8-diaza-spiro[4.5]decan-1-one rac-4-(4-Fluoro-phenyl)-8-(2-hydroxy-cyclohexyl)-2,8-diaza-spiro[4.5]decan-1-one a) As described for building block 15 step a,1, rac-4-(4-fluoro-phenyl)-2,8-diaza-spiro[4.5]decan-1-one (8.45 g, 34.0 mmol) was converted to the title compound (11.63 g, 99%) which was obtained as an off-white solid. MS: m/e=347.0 (M+H).

rac-4-(4-Fluoro-phenyl)-8-(2-oxo-cyclohexyl)-2,8-diaza-spiro[4.5]decan-1-one b) As described for building block 15 step b, 4-(4-fluoro-phenyl)-8-(2-hydroxy-cyclohexyl)-2,8-diaza-spiro[4.5]decan-1-one (2.06 g, 6.0 mmol) was converted to the title compound (1.26 g, 59%) which was obtained as a light yellow solid after purification by chromatography on silica gel eluting with DCM:MeOH (95:5 to 85:15). MS: m/e=345.2 (M+H).

EXAMPLE 11

8-[2-(4-Fluoro-phenyl)-2-hydroxy-cyclohexyl]-4-phenyl-2,8-diaza-spiro[4.5]decan-1-one To a solution of 1-bromo-4-fluorobenzene (1.4 g, 8 mmol) in dry THF (5 mL) under argon at −78° C. was added BuLi (1.6 M in hexanes, 5 mL, 8 mmol) and the mixture maintained at this temperature for 1 h. To this solution was added a solution of 8-(2-oxo-cyclohexyl)-4-phenyl-2,8-diaza-spiro[4.5]decan-1-one (687 mg, 2 mmol) in dry THF (15 mL) and the reaction mixture allowed to warm up to −20° C. after 2 h before ammonium chloride (saturated, 20 mL) was added. The resulting mixture was then evaporated and water (20 mL) added. The product was extracted with ethyl acetate (3×15 mL) and the combined organic extracts washed with brine (10 mL), dried over sodium sulfate, filtered and evaporated to leave a light brown solid. Purification by chromatography on silica gel eluting with DCM:MeOH—NH$_4$OH (0.5%) (95:5 to 4:1) afforded the title compound (380 mg, 45%) which was obtained as a white solid. MS: m/e=423.5 (M+H).

EXAMPLE 12

8-[2-(3-Fluoro-phenyl)-2-hydroxy-cyclohexyl]-4-phenyl-2,8-diaza-spiro[4.5]decan-1-one As described for example 11, 8-(2-oxo-cyclohexyl)-4-phenyl-2,8-diaza-spiro[4.5]decan-1-one (500 mg, 1.53 mmol) was converted to the title compound (348 mg, 50%) (using 3-bromo-fluorobenzene instead of 1-bromo-4-fluorobenzene) which was obtained as a white solid. MS: m/e=423.4 (M+H).

EXAMPLE 13

8-[2-Hydroxy-2-(4-methoxy-phenyl)-cyclohexyl]-4-phenyl-2,8-diaza-spiro[4.5]decan-1-one As described for example 11, 8-(2-oxo-cyclohexyl)-4-phenyl-2,8-diaza-spiro[4.5]decan-1-one (500 mg, 1.53 mmol) was converted to the title compound (88 mg, 15%) (using 4-bromoanisole instead of 1-bromo-4-fluorobenzene) which was obtained as a white solid. MS: m/e=435.6 (M+H).

EXAMPLE 14

8-[2-Hydroxy-2-(3-methoxy-phenyl)-cyclohexyl]-4-phenyl-2,8-diaza-spiro[4.5]decan-1-one As described for example 11, 8-(2-oxo-cyclohexyl)-4-phenyl-2,8-diaza-spiro[4.5]decan-1-one (500 mg, 1.53 mmol) was converted to the title compound (411 mg, 69%) (using 3-bromoanisole instead of 1-bromo-4-fluorobenzene) which was obtained as a white solid. MS: m/e=435.4 (M+H).

EXAMPLE 15

4-(4-Fluoro-phenyl)-8-[2-(3-fluoro-phenyl)-2-hydroxy-cyclohexyl]-2,8-diaza-spiro[4.5]decan-1-one As described for example 11, 4-(4-fluoro-phenyl)-8-(2-oxo-cyclohexyl)-2,8-diaza-spiro[4.5]decan-1-one (200 mg, 1 mmol) was converted to the title compound (195 mg, 76%) (using 1-bromo-3-fluorobenzene instead of 1-bromo-4-fluorobenzene) which was obtained as a white solid.

EXAMPLE 16

4-(4-Fluoro-phenyl)-8-[2-(2-fluoro-phenyl)-2-hydroxy-cyclohexyl]-2,8-diaza-spiro[4.5]decan-1-one As described for example 11, 4-(4-fluoro-phenyl)-8-(2-oxo-cyclohexyl)-2,8-diaza-spiro[4.5]decan-1-one (200 mg, 1 mmol) was converted to the title compound (178 mg, 70%) (using 2-bromofluorobenzene instead of 1-bromo-4-fluorobenzene) which was obtained as a white solid. MS: m/e=441.2 (M+H).

EXAMPLE 17

8-[2-(3-Chloro-phenyl)-2-hydroxy-cyclohexyl]-4-(4-fluoro-phenyl)-2,8-diaza-spiro[4.5]decan-1-one As described for example 11, 4-(4-fluoro-phenyl)-8-(2-oxo-cyclohexyl)-2,8-diaza-spiro[4.5]decan-1-one (200 mg, 1 mmol) was converted to the title compound (205 mg, 77%) (using 1-bromo-3-chlorobenzene instead of 1-bromo-4-fluorobenzene) which was obtained as a white solid. MS: m/e=457.3 (M).

EXAMPLE 18

4-{2-[4-(4-Fluoro-phenyl)-1-oxo-2,8-diaza-spiro[4.5]dec-8-yl]-1-hydroxy-cyclohexyl}-benzonitrile As described for example 11, 4-(4-fluoro-phenyl)-8-(2-oxo-cyclohexyl)-2,8-diaza-spiro[4.5]decan-1-one (200 mg, 1 mmol) was converted to the title compound (118 mg, 45%) (using 4-bromobenzonitrile instead of 1-bromo-4-fluorobenzene) which was obtained as a white solid. MS: m/e=448.2 (M+H).

EXAMPLE 19

4-(4-Fluoro-phenyl)-8-[2-hydroxy-2-(4-trifluoromethyl-phenyl)-cyclohexyl]-2,8-diaza-spiro[4.5]decan-1-one As described for example 11, 4-(4-fluoro-phenyl)-8-(2-oxo-cyclohexyl)-2,8-diaza-spiro[4.5]decan-1-one (200 mg, 1 mmol) was converted to the title compound (271 mg, 95%) (using 4-bromobenzotrifluoride instead of 1-bromo-4-fluorobenzene) which was obtained as a white solid. MS: m/e 491.2 (M+H).

EXAMPLE 20

4-(4-Fluoro-phenyl)-8-[2-hydroxy-2-(4-methanesulfonyl-phenyl)-cyclohexyl]-2,8-diaza-spiro[4.5]decan-1-one As described for example 11, 4-(4-fluoro-phenyl)-8-(2-oxo-cyclohexyl)-2,8-diaza-spiro[4.5]decan-1-one (200 mg, 1 mmol) was converted to the title compound (16 mg, 6%) (using 4-bromophenylmethyl sulfone instead of 1-bromo-4-fluorobenzene) which was obtained as a white solid. MS: m/e=501.5 (M+H).

EXAMPLE 21

4-(4-Fluoro-phenyl)-8-(2-hydroxy-2-p-tolyl-cyclohexyl)-2,8-diaza-spiro[4.5]decan-1-one As described for example 11, 4-(4-fluoro-phenyl)-8-(2-oxo-cyclohexyl)-2,8-diaza-spiro[4.5]decan-1-one (200 mg, 1 mmol) was converted to the title compound (178 mg, 70%) (using 4-bromotoluene instead of 1-bromo-4-fluorobenzene) which was obtained as a white solid. MS: m/e=437.4 (M+H).

EXAMPLE 22

4-(4-Fluoro-phenyl)-8-(2-hydroxy-2-m-tolyl-cyclohexyl)-2,8-diaza-spiro[4.5]decan-1-one As described for example 11, 4-(4-fluoro-phenyl)-8-(2-oxo-cyclohexyl)-2,8-diaza-spiro[4.5]decan-1-one (200 mg, 1 mmol) was converted to the title compound (229 mg, 90%) (using 3-bromotoluene instead of 1-bromo-4-fluorobenzene) which was obtained as a white solid. MS: m/e=437.3 (M+H).

EXAMPLE 23

4-(4-Fluoro-phenyl)-8-(2-hydroxy-2-o-tolyl-cyclohexyl)-2,8-diaza-spiro[4.5]decan-1-one As described for example 11, 4-(4-fluoro-phenyl)-8-(2-oxo-cyclohexyl)-2,8-diaza-spiro[4.5]decan-1-one (200 mg, 1 mmol) was converted to the title compound (158 mg, 62%) (using 2-bromotoluene instead of 1-bromo-4-fluorobenzene) which was obtained as a white solid. MS: m/e=437.4 (M+H).

EXAMPLE 24

8-[2-(4-tert-Butyl-phenyl)-2-hydroxy-cyclohexyl]-4-(4-fluoro-phenyl)-2,8-diaza-spiro[4.5]decan-1-one As described for example 11, 4-(4-fluoro-phenyl)-8-(2-oxo-cyclohexyl)-2,8-diaza-spiro[4.5]decan-1-one (200 mg, 1 mmol) was converted to the title compound (192 mg, 69%) (using 1-bromo-4-tert-butylbenzene instead of 1-bromo-4-fluorobenzene) which was obtained as a white solid. MS: m/e=479.6 (M+H).

EXAMPLE 25

4-(4-Fluoro-phenyl)-8-[2-hydroxy-2-(2-trifluoromethoxy-phenyl)-cyclohexyl]-2,8-diaza-spiro[4.5]decan-1-one As described for example 11, 4-(4-fluoro-phenyl)-8-(2-oxo-cyclohexyl)-2,8-diaza-spiro[4.5]decan-1-one (216 mg, 0.63 mmol) was converted to the title compound (209 mg, 66%) (using 1-bromo-2-(trifluoromethoxy)benzene instead of 1-bromo-4-fluorobenzene) which was obtained as a white solid. MS: m/e=507.3 (M+H).

EXAMPLE 26

4-(4-Fluoro-phenyl)-8-[2-hydroxy-2-(4-imidazol-1-yl-phenyl)-cyclohexyl]-2,8-diaza-spiro[4.5]decan-1-one As described for example 11, 4-(4-fluoro-phenyl)-8-(2-oxo-cyclohexyl)-2,8-diaza-spiro[4.5]decan-1-one (344 mg, 1.0 mmol) was converted to the title compound (231 mg, 47%) (using 1-(4-bromophenyl)imidazole instead of 1-bromo-4-fluorobenzene) which was obtained as a white solid. MS: m/e=489.3 (M+H).

EXAMPLE 27

4-(4-Fluoro-phenyl)-8-[2-hydroxy-2-(4-methoxy-phenyl)-cyclohexyl]-2,8-diaza-spiro[4.5]decan-1-one As described for example 11, 4-(4-fluoro-phenyl)-8-(2-oxo-cyclohexyl)-2,8-diaza-spiro[4.5]decan-1-one (517 mg, 1.5 mmol) was converted to the title compound (568 mg, 84%) (using 4-bromoanisole instead of 1-bromo-4-fluorobenzene) which was obtained as a white solid. MS: m/e=453.3 (M+H).

EXAMPLE 28

4-(4-Fluoro-phenyl)-8-[2-hydroxy-2-(3-methoxy-phenyl)-cyclohexyl]-2,8-diaza-spiro[4.5]decan-1-one As described for example 11, 4-(4-fluoro-phenyl)-8-(2-oxo-cyclohexyl)-2,8-diaza-spiro[4.5]decan-1-one (200 mg, 1 mmol) was converted to the title compound (199 mg, 76%) (using 3-bromoanisole instead of 1-bromo-4-fluorobenzene) which was obtained as a white solid. MS: m/e=453.3 (M+H).

EXAMPLE 29

4-(4-Fluoro-phenyl)-8-trans-(4-hydroxy-4-phenyl-tetrahydro-pyran-3-yl)-2,8-diaza-spiro[4.5]decan-1-one 4-(4-Fluoro-phenyl)-8-trans-(4-hydroxy-tetrahydro-pyran-3-yl)-2,8-diaza-spiro[4.5]decan-1-one a) As described for example 12a, (R)-4-(4-fluoro-phenyl)-8-(2-oxo-cyclohexyl)-2,8-diaza-spiro[4.5]decan-1-one (100 mg, 0.4 mmol) was converted to the title compound (57 mg, 41%) (using 3,5-epoxytetrahydrofuran instead of oxa-bicyclo[4.1.0]heptane) which was obtained as a white solid after purification by chromatography on silica gel eluting with DCM: MeOH (9:1). MS: m/e=349.2 (M+H).

4-(4-Fluoro-phenyl)-8-(4-oxo-tetrahydro-pyran-3-yl)-2,8-diaza-spiro[4.5]decan-1-one b) As described for building block 11 step bi) 4-(4-fluoro-phenyl)-8-trans-(4-hydroxy-tetrahydro-pyran-3-yl)-2,8-diaza-spiro[4.5]decan-1-one (128 mg, 0.37 mmol) was converted to the title compound (100 mg, 79%) which was obtained as a white solid after purification by chromatography on silica gel eluting with DCM: MeOH (9:1). MS: m/e=347.4 (M+H).

4-(4-Fluoro-phenyl)-8-trans-(4-hydroxy-4-phenyl-tetrahydro-pyran-3-yl)-2,8-diaza-spiro[4.5]decan-1-one c) As described for example 11, 4-(4-fluoro-phenyl)-8-(4-oxo-tetrahydro-pyran-3-yl)-2,8-diaza-spiro[4.5]decan-1-one (90 mg, 0.26 mmol) was converted to the title compound (65 mg, 59%) (using phenyllithium instead of 1-bromo-4-fluorobenzene) which was obtained as a white solid. MS: m/e=425.4 (M+H).

| n | X | A-B | R¹ | R³ | R² | Example |
|---|---|---|---|---|---|---|
| 1 | H | CH₂CH₂ | 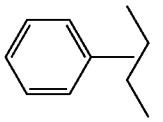 | H | 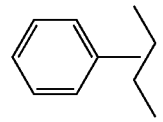 | 1 |
| 1 | H | CH₂CH₂ | 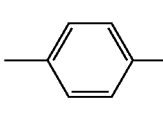 | H | 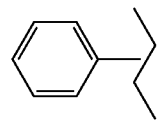 | 2 |

-continued
| n | X | A-B | R¹ | R³ | R² | Example |
|---|---|---|---|---|---|---|
| 1 | H | CH$_2$CH$_2$ | 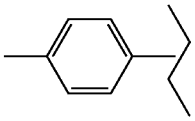 | H | 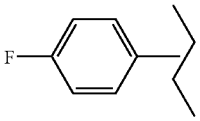 | 3 |
| 1 | H | CH$_2$CH$_2$ | 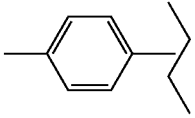 | H | 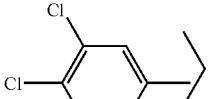 | 4 |
| 1 | H | CH$_2$CH$_2$ | 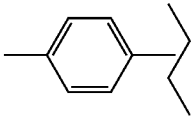 | H | 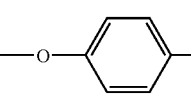 | 5 |
| 1 | H | CH$_2$CH$_2$ | 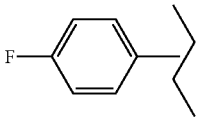 | H | 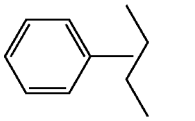 | 6 |
| 1 | H | CH$_2$CH$_2$ | 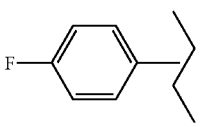 | H | 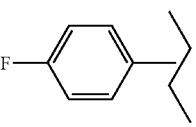 | 7 |
| 1 | H | CH$_2$CH$_2$ | 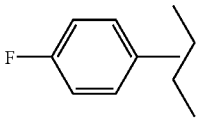 | H | 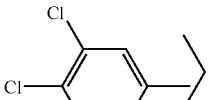 | 8 |
| 1 | H | CH$_2$CH$_2$ | 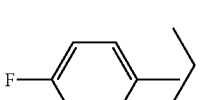 | H | 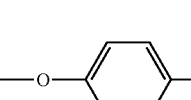 | 9 |
| 1 | H | CH$_2$CH$_2$ | 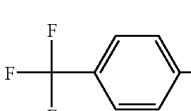 | H | 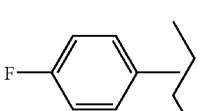 | 10 |
| 1 | OH | CH$_2$CH$_2$ | 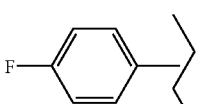 | H | 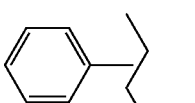 | 11 |
| 1 | OH | CH$_2$CH$_2$ | 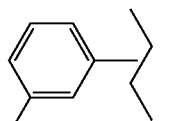 | H | 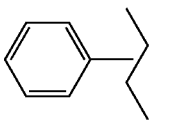 | 12 |
| 1 | OH | CH$_2$CH$_2$ | 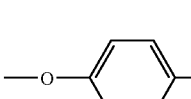 | H | 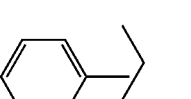 | 13 |

-continued
| n | X | A-B | R¹ | R³ | R² | Example |
|---|---|---|---|---|---|---|
| 1 | OH | CH₂CH₂ | 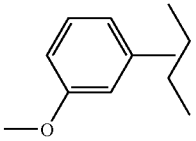 | H | 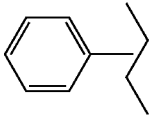 | 14 |
| 1 | OH | CH₂CH₂ | 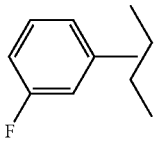 | H | 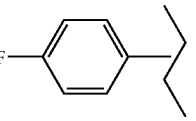 | 15 |
| 1 | OH | CH₂CH₂ | 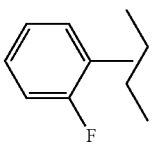 | H | 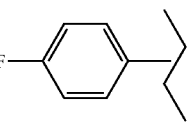 | 16 |
| 1 | OH | CH₂CH₂ | 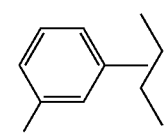 | H | 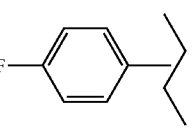 | 17 |
| 1 | OH | CH₂CH₂ | 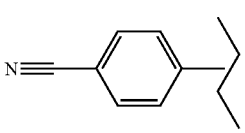 | H | 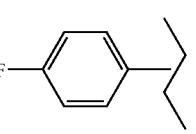 | 18 |
| 1 | OH | CH₂CH₂ | 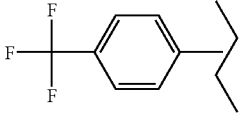 | H | 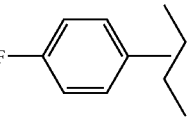 | 19 |
| 1 | OH | CH₂CH₂ | 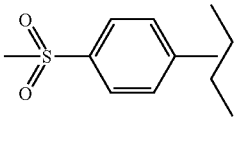 | H | 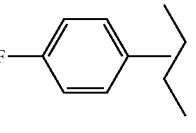 | 20 |
| 1 | OH | CH₂CH₂ | 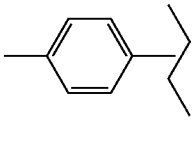 | H | 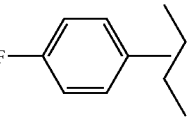 | 21 |
| 1 | OH | CH₂CH₂ | 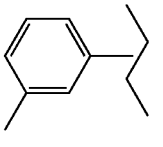 | H | 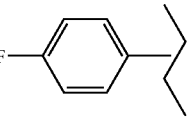 | 22 |
| 1 | OH | CH₂CH₂ | 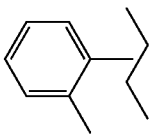 | H | 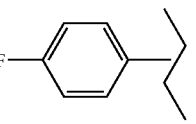 | 23 |

-continued

| n | X | A-B | R¹ | R³ | R² | Example |
|---|----|-----|----|----|-----|---------|
| 1 | OH | CH₂CH₂ | 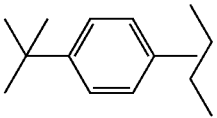 | H | 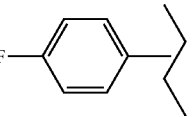 | 24 |
| 1 | OH | CH₂CH₂ | 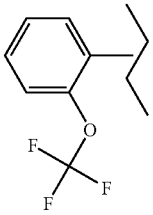 | H | 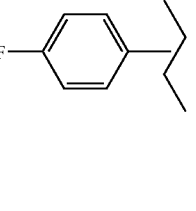 | 25 |
| 1 | OH | CH₂CH₂ | 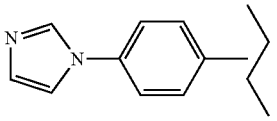 | H | 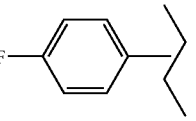 | 26 |
| 1 | OH | CH₂CH₂ | 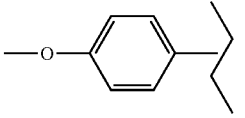 | H | 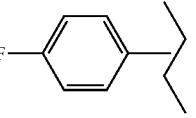 | 27 |
| 1 | OH | CH₂CH₂ | 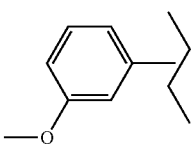 | H | 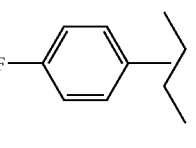 | 28 |
| 1 | OH | CH₂O | 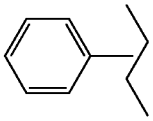 | H | 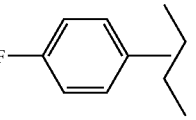 | 29 |

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The invention claimed is:
1. A compound of formula I

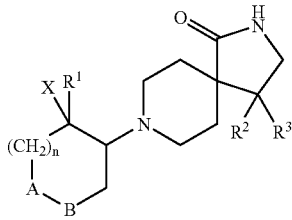

wherein
A-B is —CH$_2$—CH$_2$—, —CH$_2$—O— or —O—CH$_2$—;
X is hydrogen or hydroxy;
R$^1$ is aryl, optionally substituted by one or two substituents selected from the group consisting of halogen, lower alkyl, cyano, CF$_3$, —OCF$_3$, lower alkoxy, —SO$_2$-lower alkyl, and heteroaryl,
R$^2$ is aryl, optionally substituted by one or two substituents selected from the group consisting of halogen, lower alkyl, CF$_3$, and lower alkoxy;
R$^3$ is hydrogen or lower alkyl;
n is 0, 1 or 2;
or a pharmaceutically active salt thereof.

2. A compound of claim 1 wherein A-B is —CH$_2$—CH$_2$— or —CH$_2$—O—.

3. A compound of claim 2, wherein R$^1$ is phenyl, optionally substituted by one or two substituents selected from the group consisting of halogen, lower alkyl, cyano, CF$_3$, —OCF$_3$, lower alkoxy, —SO$_2$-lower alkyl, and heteroaryl.

4. A compound of claim 3, wherein R$^2$ is phenyl, optionally substituted by one or two substituents selected from the group consisting of halogen and lower alkoxy.

5. A compound of claim 4, wherein R$^3$ is hydrogen.

6. A compound of claim 5, wherein n is 1.

7. A compound of claim 3, wherein R$^1$ is phenyl.

8. A compound of claim 2, wherein A-B is —CH$_2$—CH$_2$—.

9. A compound of claim 8, wherein R$^1$ and R$^2$ are both phenyl, optionally substituted by lower alkyl, halogen or CF$_3$.

10. A compound of claim 9, selected from the group consisting of
cis-rac-4-phenyl-8-(2-phenyl-cyclohexyl)-2,8-diaza-spiro[4.5]decan-1-one,
cis-rac-4-phenyl-8-(2-p-tolyl-cyclohexyl)-2,8-diaza-spiro[4.5]decan-1-one,
cis-rac-8-[2-(4-fluoro-phenyl)-cyclohexyl]-4-phenyl-2,8-diaza-spiro[4.5]decan-1-one,
cis-rac-4-(4-fluoro-phenyl)-8-[2-(4-fluoro-phenyl)-cyclohexyl]-2,8-diaza-spiro[4.5]decan-1-one,
cis-rac-4-(4-fluoro-phenyl)-8-[2-(4-trifluoromethyl-phenyl)-cyclohexyl]-2,8-diaza-spiro[4.5]decan-1-one,
8-[2-(4-fluoro-phenyl)-2-hydroxy-cyclohexyl]-4-phenyl-2,8-diaza-spiro[4.5]decan-1-one,
4-(4-fluoro-phenyl)-8-[2-(3-fluoro-phenyl)-2-hydroxy-cyclohexyl]-2,8-diaza-spiro[4.5]decan-1-one,
4-(4-fluoro-phenyl)-8-[2-(2-fluoro-phenyl)-2-hydroxy-cyclohexyl]-2,8-diaza-spiro[4.5]decan-1-one,
8-[2-(3-chloro-phenyl)-2-hydroxy-cyclohexyl]-4-(4-fluoro-phenyl)-2,8-diaza-spiro[4.5]decan-1-one, and
4-(4-fluoro-phenyl)-8-trans-(4-hydroxy-4-phenyl-tetrahydro-pyran-3-yl)-2,8-diaza-spiro[4.5]decan-1-one.

11. A compound of claim 8, wherein n is 1.
12. A compound of claim 2, wherein A-B is —CH$_2$—O—.
13. A compound of claim 12, wherein R$^1$ and R$^2$ are both phenyl, optionally substituted by lower alkyl, halogen or CF$_3$.
14. A compound of claim 12, wherein n is 1.
15. A compound of claim 2 wherein R$^2$ is phenyl, optionally substituted by one or two substituents selected from the group consisting of halogen and lower alkoxy.
16. A compound of claim 15, wherein R$^2$ is phenyl.
17. A compound of claim 1, wherein X is hydrogen.
18. A compound of claim 17, wherein R$^1$ is phenyl, optionally substituted by one or two substituents selected from the group consisting of halogen, lower alkyl, cyano, CF$_3$, —OCF$_3$, lower alkoxy, —SO$_2$-lower alkyl, and heteroaryl.
19. A compound of claim 17 wherein R$^2$ is phenyl, optionally substituted by one or two substituents selected from the group consisting of halogen and lower alkoxy.
20. A compound of claim 17, wherein R$^3$ is hydrogen.
21. A compound of claim 17, wherein R$^3$ is lower alkyl.
22. A compound of claim 17, wherein n is 1.
23. A compound of claim 17, wherein A-B is —CH$_2$—O—.
24. A compound of claim 17, wherein A-B is —CH$_2$—CH$_2$—.
25. A compound of claim 1, wherein X is hydroxy.
26. A compound of claim 25, wherein R$^1$ is phenyl, optionally substituted by one or two substituents selected from the group consisting of halogen, lower alkyl, cyano, CF$_3$, —OCF$_3$, lower alkoxy, —SO$_2$-lower alkyl, and heteroaryl.
27. A compound of claim 25, wherein R$^2$ is phenyl, optionally substituted by one or two substituents selected from the group consisting of halogen and lower alkoxy.
28. A compound of claim 25, wherein R$^3$ is hydrogen.
29. A compound of claim 25, wherein R$^3$ is lower alkyl.
30. A compound of claim 25, wherein n is 1.
31. A compound of claim 25, wherein A-B is —CH$_2$—CH$_2$—.
32. A compound of claim 25, wherein A-B is —CH$_2$—O—.
33. A compound of claim 1, wherein R$^3$ is hydrogen.
34. A compound of claim 1, wherein R$^3$ is lower alkyl.
35. A compound of claim 1, wherein A-B is —O—CH$_2$—.
36. A compound of claim 35, wherein R$^1$ and R$^2$ are both phenyl, optionally substituted by lower alkyl, halogen or CF$_3$.
37. A compound of claim 1, wherein R$^1$ is phenyl, optionally substituted by one or two substituents selected from the group consisting of halogen, lower alkyl, cyano, CF$_3$, —OCF$_3$, lower alkoxy, —SO$_2$-lower alkyl, and heteroaryl.
38. A compound of claim 37, wherein R$^2$ is phenyl, optionally substituted by one or two substituents selected from the group consisting of halogen and lower alkoxy.
39. A compound of claim 37, wherein R$^1$ and R$^2$ are both phenyl, optionally substituted by lower alkyl, halogen or CF$_3$.
40. A compound of claim 37, wherein n is 1.
41. A compound of claim 37, wherein X is hydrogen.
42. A compound of claim 37, wherein X is hydroxy.
43. A compound of claim 37, wherein R$^3$ is hydrogen.
44. A compound of claim 37, wherein R$^3$ is lower alkyl.
45. A compound of claim 37, wherein A-B is —CH$_2$—CH$_2$—.

46. A compound of claim 1, wherein $R^2$ is phenyl, optionally substituted by one or two substituents selected from the group consisting of halogen and lower alkoxy.

47. A compound of claim 46, wherein n is 1.

48. A compound of claim 46, wherein X is hydrogen.

49. A compound of claim 46, wherein X is hydroxy.

50. A compound of claim 46, wherein X is hydrogen.

51. A compound of claim 46, wherein $R^3$ is lower alkyl.

52. A compound of claim 46, wherein A-B is —$CH_2$—$CH_2$—.

* * * * *